US009536307B2

(12) United States Patent
Kabus et al.

(10) Patent No.: US 9,536,307 B2
(45) Date of Patent: Jan. 3, 2017

(54) REGISTRATION OF MEDICAL IMAGES (71) Applicant: KONINKLIJKE PHILIPS N.V., Eindhoven (NL)

(72) Inventors: Sven Kabus, Hamburg (DE); Heike Ruppertshofen, Hamburg (DE); Holger Schmitt, Luetjensee (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/763,853

(22) PCT Filed: Oct. 14, 2014

(86) PCT No.: PCT/EP2014/071934
§ 371 (c)(1),
(2) Date: Jul. 28, 2015

(87) PCT Pub. No.: WO2015/055599
PCT Pub. Date: Apr. 23, 2015

(65) Prior Publication Data
US 2016/0217576 A1    Jul. 28, 2016

(30) Foreign Application Priority Data
Oct. 18, 2013   (EP) .................................... 13189219

(51) Int. Cl.
G06T 7/00       (2006.01)
A61B 6/00       (2006.01)
(Continued)

(52) U.S. Cl.
CPC ............. G06T 7/0024 (2013.01); A61B 5/055 (2013.01); A61B 6/032 (2013.01); A61B 6/037 (2013.01);
(Continued)

(58) Field of Classification Search
CPC .... G06T 3/0068; G06T 7/0012; G06T 7/0024; G06T 7/0028; G06T 2207/20016; G06T 2207/20092
See application file for complete search history.

(56) References Cited

U.S. PATENT DOCUMENTS 7,231,076 B2    6/2007    Fu et al. ........................ 382/131
7,778,490 B2    8/2010    Quist ............................. 382/294
(Continued)

FOREIGN PATENT DOCUMENTS

JP    2002032735 A    1/2002
JP    2007520762 A    7/2007
(Continued)

OTHER PUBLICATIONS

Klein, et al., "A Comparison of Acceleration Techniques for Non-rigid Medical Image Registration", Jan. 1, 2006.
(Continued)

*Primary Examiner* — Andrew W Johns (57) ABSTRACT

The invention relates to a method and an image processing device (50) for the registration of two images ($I_1$, $I_2$) that may for example be provided by a CT scanner (10) and/or an MRI scanner (20). According to one embodiment of the invention, the images are first globally registered (GR) with a given registration algorithm using a first parameter vector (p). A user may then select a region of interest ROI, and a plurality of local registrations (LR1, . . . LRs, . . . LRn) are calculated for this ROI using the same registration algorithm but different parameter vectors (p, p, . . . p). The results of the local registrations (LR1, . . . LRs, . . . LRn) are displayed and the user can select the best local registration(s). In a final step, the selected local registration(s) (LRs) and the global registration (GR) may be merged. Additionally or alterna-
(Continued)

tively, a parameter vector for a local registration in the ROI may be determined by an automatic analysis of the ROI.

28 Claims, 3 Drawing Sheets

(51) Int. Cl.
| | |
|---|---|
| G06T 3/00 | (2006.01) |
| A61B 5/055 | (2006.01) |
| A61B 6/03 | (2006.01) |
| A61B 8/00 | (2006.01) |
| G01R 33/48 | (2006.01) |
| G01R 33/56 | (2006.01) |

(52) U.S. Cl.
CPC ............ *A61B 6/469* (2013.01); *A61B 6/5247* (2013.01); *A61B 8/00* (2013.01); *G06T 3/0068* (2013.01); *G06T 7/0012* (2013.01); *G06T 7/0081* (2013.01); *G01R 33/4812* (2013.01); *G01R 33/5608* (2013.01); *G06T 2207/20012* (2013.01); *G06T 2207/20092* (2013.01); *G06T 2207/20104* (2013.01); *G06T 2207/30004* (2013.01)

(56) References Cited

U.S. PATENT DOCUMENTS

| | | | |
|---|---|---|---|
| 8,380,007 B2 | 2/2013 | Chan et al. | 382/294 |
| 8,977,027 B2 | 3/2015 | Da Silva et al. | G06T 11/003 |
| 2005/0065421 A1 | 3/2005 | Burckhardt | 600/407 |
| 2010/0235352 A1 | 9/2010 | Slutsky et al. | 707/723 |
| 2013/0182925 A1 | 7/2013 | Razeto et al. | 382/131 |
| 2014/0003690 A1 | 1/2014 | Razeto et al. | 382/131 |

FOREIGN PATENT DOCUMENTS

| | | |
|---|---|---|
| JP | 2012034069 A | 2/2012 |
| WO | 2004063990 A1 | 7/2004 |
| WO | 2006011935 A2 | 2/2006 |
| WO | 2007066294 A2 | 6/2007 |
| WO | 2012025855 A1 | 3/2012 |

OTHER PUBLICATIONS

Maintz, J. B. A., et al.; A Survey of Medical Image Registration; 1998; Medical Image Analysis; 2(1)1-37.

Murphy, K., et al.; Semi-automatic construction of reference standards for evaluation of image registration; 2011; Medical Image Analysis; 15:71-84.

Modersitzki, J., et al.; Numerical methods for vol. preserving image registration; 2004; Inverse Problems; 20(5)1621.

Rueckert, D., et al.; Nonrigid registration using free-form deformations: application to breast MR images; 1999; IEEE Trans. on Medical Imaging; 18(8)712-721, (abstract only).

REGISTRATION OF MEDICAL IMAGES

FIELD OF THE INVENTION

The invention relates to a method and an image processing device for the registration of at least two images of an object, for example of CT and/or MRI scans of the body of a patient.

BACKGROUND OF THE INVENTION

The US 2013/0182925 A1 discloses a method of initially registering a first set of image data and a second set of image data. A further registration of the images is then performed in a region that is automatically or manually selected. The initial registration may for example be a free-form transformation, while the further registration is a rigid registration. In a final step, the initial and the further registrations may be merged.

The US 2005/065421 A1 discloses a method in which first anatomical and functional images are co-registered, and second anatomical and functional images, acquired at a later stage, are co-registered. A global, rigid registration is performed on the first and second anatomical images. Moreover, a volume of interest (ROI) is identified in the first co-registered composite image data set and a local, non-rigid registration is performed on this ROI and a corresponding ROI within the globally registered image data set.

The WO 2007/066294 A2 discloses a procedure in which several registrations of a first image and a second image are displayed on a display during a medical intervention. A physician can then visually select one of the registrations for subsequent use.

The WO 20121025855 A1 discloses the registration of anatomical images and emission images. In one embodiment, a global rigid registration is followed by a local non-rigid registration of a region of interest.

SUMMARY OF THE INVENTION

In view of the above, it would be desirable to have means that allow for an improved registration of images.

This object is addressed by an image processing device according to claim 1, a method according to claim 2, and a medical imaging apparatus according to claim 3. Preferred embodiments are disclosed in the dependent claims.

According to a first aspect, an embodiment of the invention relates to an image processing device that can register at least two images of an object, said device comprising the following components:

A first module that is called "global registration module" in the following and that serves for executing a registration (called "global registration") of the at least two images using a given registration algorithm with a first parameter vector.

A second module that is called "selection module" in the following and that serves for the selection of a given region of interest, called "ROI", in the images.

A third module that is called "local registration module" in the following and that serves for executing at least one registration (called "local registration") of the images within the selected ROI using the above-mentioned given registration algorithm with a parameter vector that is different from the first parameter vector.

Moreover, the aforementioned "different parameter vector" of the local registration is automatically determined for at least one local registration based on an automatic analysis of the ROI, wherein said analysis comprises at least one of the following items: the evaluation of intensity ranges, image edges, entropy measurements, intensity histograms, edge histograms, intensity range of residuum, and/or anatomical position.

The image processing device may for example be realized by dedicated electronic hardware, digital data processing hardware with associated software, or a mixture of both.

The images that are processed by the device are typically two-dimensional or three-dimensional images, for example obtained from a medical CT (Computed Tomography) or MRI (Magnetic Resonance Imaging) scanning procedure. The images are preferably encoded as digital data sets in which each element represents an image value (e.g. a gray value) at an associated point in space (represented e.g. by its x, y, z-coordinates in an associated coordinate system).

As usual, the "registration" of two images of an object refers to the determination of a mapping between the two images that maps each image point of a first one of the images onto that image point of the second image which belongs to the same location or structure of the imaged object. A registration of images that have been generated with the same apparatus is usually necessary because of possible movements of the object (motion of a patient; heart beat; growth of a structure etc.). Registration of images that have been generated with different apparatuses/modalities is usually necessary because one and the same structure of the imaged object is represented differently in such images. Prior to a registration, images may be preprocessed appropriately, for example by a filtering or by the removal of objects that are of no interest.

The object that is depicted in the processed images may for example be (a part of) the body of a person or animal in medical examinations, a suitcase in baggage control, a piece of material in material sciences or the like.

The attributes "global" and "local" shall indicate that the "global registration" extends to a larger part of the images than the "local registration", the latter being restricted to the selected ROI. It is however possible that the "global registration" does not cover the whole images, for example if structures of no interest are left out (e.g. the patient table).

The "given registration algorithm" may be any algorithm that is appropriate for the desired registration of the images at hand. A variety of such registration algorithms are known in the art, for example rigid registrations, affine registrations, and non-rigid registrations (cf. US 2013/0182925 A1; J. Modersitzki, "Numerical Methods for Image Registration". Oxford University Press, 2004; D. Rueckert, L. I. Sonoda, C. Hayes, D. L. G. Hill, M. O. Leach, and D. J. Hawkes, "Non-rigid registration using free-form deformations: Application to breast MR images", IEEE Transactions on Medical Imaging, 18(8):712-721, 1999). All that is assumed about the used registration algorithm is that it depends on $N \geq 1$ parameters, wherein these parameters can be arranged in a "parameter vector" of some N-dimensional parameter space.

If more than one local registration is executed by the local registration module, each of them will use a parameter vector that is different from both the first parameter vector and from the parameter vectors of the other local registrations.

The selection of the ROI may be executed in any one of the original images, in both images simultaneously (with a later merging of the selections), and/or in the globally registered version of the images. The latter option is typically preferred as the globally registered images reveal those areas where the global registration may not yet be good enough such that these areas can be selected as ROI.

Moreover, the selection of a ROI and the corresponding determination of at least one local registration can optionally be repeated several times for different ROIs and/or be executed in parallel for different ROIs.

The at least one local registration may be performed with the original images or, preferably, by using the globally registered images as starting point.

According to a second aspect, an embodiment of the invention relates to a method for the registration of at least two images of an object, said method comprising the following steps that may be executed in the listed or any other order or in parallel, if appropriate:

a) A "global registration" of the images using a given registration algorithm with a first parameter vector.
b) The selection of a region of interest, called ROI, in the images.
c) At least one "local registration" of the images within the selected ROI using the given registration algorithm with a different parameter vector.

Moreover, the aforementioned "different parameter vector" of the local registration is automatically determined for at least one local registration based on an automatic analysis of the ROI, wherein said analysis comprises at least one of the following items: the evaluation of intensity ranges, image edges, entropy measurements, intensity histograms, edge histograms, intensity range of residuum, and/or anatomical position.

According to a third aspect, an embodiment of the invention relates to a medical imaging apparatus comprising the following components:

At least one image generating device for generating images of an object.

An image processing device of the kind described above for the registration of images provided by the image generating device. The image processing device will hence comprise a global registration module for executing a global registration of the images using a given registration algorithm with a first parameter vector, a selection module for the selection of a ROI in the images, and a local registration module for executing at least one local registration of the images within the selected ROI using the given registration algorithm with a different parameter vector.

The image processing device, the method, and the medical imaging apparatus are based on the same concept that a global registration of two images is followed by at least one local registration with a different parameter vector in a selected region of interest. Explanations provided for one of these embodiments are therefore valid for the other embodiments, too.

The image processing device, the method, and the medical imaging apparatus have the advantage that they allow for an effective improvement of the registration of two images that can readily be implemented. This is because a first registration, which would usually be taken as the final result, is locally refined in at least one selected region of interest by a local registration. As said local registration applies the same registration algorithm as the first registration, the refinement can be achieved without a need of implementing a completely different registration algorithm.

In the following, various preferred embodiments of the invention will be described that can be realized in connection with the image processing device, the method, and the medical imaging apparatus described above.

In a first preferred basic embodiment, at least two local registrations are executed with different parameter vectors (with respect to the image processing device, this means that the local registration module is designed to execute at least two registrations with different parameter vectors). The different parameter vectors may be given in advance, for example provided from a memory of the local registration module. Additionally or alternatively, they may be chosen or generated (i) at random, (ii) based on user inputs, and/or (iii) in dependence on the selected ROI and/or the type of the images to be registered. Calculation of two or more local registrations allows for a comparison of the results, for example with the help of some objective function that provides a numerical score for the results. The best of the local registrations can then be chosen for further usage.

In a further development of the aforementioned approach, the results of the local registrations with different parameter vectors are displayed (e.g. on a monitor of the image processing device or the medical imaging apparatus), wherein a user can then select at least one of the displayed results for further usage. The selection may for example be done with the help of some input device such as a mouse, a trackball, a keyboard or the like (again, this may be a part of the image processing device and/or the medical imaging apparatus). Typically, the user will select the local registration that appears to be the best, though other selection criteria are possible, too. Displaying of the result of a registration may be done in any appropriate way, for example by showing an overlay of the registered images. The selection of a result of a local registration is of course tantamount to the selection of a particular local registration and its parameter vector that has been used for achieving the selected result. The results of the local registrations may be displayed sequentially, perhaps with the additional option for the user to jump between the results. Most preferably, the results of the local registrations are displayed simultaneously such that the user can see them at a glance and compare them in parallel. Additionally or alternatively, the result of the global registration may be displayed in parallel, too.

The aforementioned selection of a local registration is advantageous in that it allows for a refinement of the image registration by exploiting the user's capabilities of (intuitively) evaluating registrations. The image processing device is used for what it can do best, i.e. executing numerical calculations (for several local registrations) with high velocity. All the user has to do is to select, for example via a simple mouse click, that one of the local registrations that appears to him/her to be the best, wherein this selection will often be based on criteria that can hardly be formulated rigorously or be implemented in an algorithm.

The user may optionally also select two or more results of the local registrations for further usage. Preferably, the user may simultaneously provide a ranking of the selected registrations ("best", "second-best", etc.). The parameter vectors of the selected registrations will then usually indicate a sub-region of the whole parameter space that can be searched with preference during a further optimization of the local registration. For example, the average of the selected parameter vectors (optionally weighted with their ranking) could be used to define a new local registration.

After the selection of one local registration from the displayed results of local registrations by a user, this selected registration may optionally be refined in a further processing step (if several local registrations have been selected, each of them may be refined and/or a new local registration that is derived from them can be refined). Hence the optimum of this selected local registration can be taken as basis for a further usage. A refinement of a local registration may for example comprise a new calculation of said local registration with a change of one or more parameters (which may be components of the associated parameter vector or not) that are known to improve the accuracy of the registration. Such parameters may for example be related to the resolution of the processed images and/or the number of iterations that are performed with an iterative registration algorithm. Usually sub-optimal values will be chosen for such parameters when several local registrations have to be calculated in order to limit the required runtime of the algorithm to reasonable values. The usage of sub-optimal, simplified local registrations is usually sufficient for the intended purpose of finding out which of the local registrations yield better results than the others.

In the above embodiment, the selection of one or more displayed results from several local registrations by a user will typically take place again and again a lot of times with different input images (e.g. from different body regions and/or patients). In such a scenario the user's selections may optionally be evaluated with respect to possible preferences, i.e. with respect to deviations from a (blind or random) selection of registrations with equal probability. For example, if the user selects parameter vectors from some sub-region of parameter space more frequently than from other regions, this indicates a preference that may be detected qualitatively or even quantitatively. This information can preferably be exploited during future image registrations. Local registrations with parameter vectors that are preferred by the user may for example be presented as default selections. Additionally or alternatively, more local registrations can be computed in a region of parameter space that comprises preferred parameter vectors. Similarly, regions of parameter space from which local registrations are seldom or never selected can be sampled more sparsely or be omitted altogether. The registration procedure can thus be provided with some kind of learning capability that provides for a continuous improvement over time. It should be noted that "the user" whose preferences are determined may of course also correspond to a group of several users.

In the image processing device, the method, and/or the medical imaging apparatus, the "different parameter vector" of the local registration is automatically determined for at least one local registration based on an automatic analysis of the ROI. In one embodiment, the user's input may be limited to the selection of the ROI (if this is not done automatically, too), and an automatic algorithm analyzes this ROI and determines some parameter vector for a local registration (e.g. according to some given criterion that is implemented in the algorithm). Due to the focusing on the ROI, the automatically determined parameter vector will usually yield better registration results (for the ROI) than the global registration which had to use the first parameter vector that was chosen in view of the WHOLE images.

The aforementioned automatic analysis of the ROI comprises at least one of the following items: the evaluation of intensity ranges, image edges, entropy measurements, intensity histograms, edge histograms, intensity range of residuum, and/or anatomical position.

As an example, the evaluation of intensity ranges for an underlying image can indicate which kind of anatomical content (for a CT image e.g. air within the lungs or bowel gas with very low HU values, liquids, non-dense or dense tissue with moderate HU values, bone structures with higher HU values) is present in the ROI and can therefore justify a certain parameter setting. The registration of bone structures will for example require a stiffer deformation while registration of tissue structures requires a moderate elasticity. The presence of air or gas can suggest a setting which allows for larger volume changes between the images to be compared.

As a further example, the evaluation of intensity histograms extends the evaluation of intensity ranges. A histogram analysis can be used to quantify the portions of certain intensity ranges (e.g. of bones and liquids). A parameter setting designed for the largest portion present in the ROI can then be chosen, or the parameter setting may be chosen sub-ROI-dependent or even voxel-dependent, e.g. if the ROI is composed of more than one material. In addition, the histogram analysis can be done separately on each image, which allows e.g. detection for contrast agent in one of the images. An adequate parameter setting for this scenario would be an elastic but volume-preserving deformation.

As another example, the evaluation of image edges, e.g. via computing gradient images, indicates if edges are present in the ROI. Image edges can be prominent (e.g. at the diaphragm) or small (e.g. at the intestine interface between liver and kidney). While prominent image edges are easy to match, edges of smaller strength may require a parameter setting with a decreased weight of the regularizer or with an increased weight of the similarity term or may require a pre-processing of the images in order to enhance the strength of the edge.

As another example, the evaluation of edge histograms extends the evaluation of image edges. A histogram analysis can be used to quantify the amount of edges with a certain strength. Similar to the scenario where intensity histograms are evaluated, dedicated parameter settings for sub-ROIs may be chosen.

As a further example, the evaluation of the residuum image can be used. Non-aligned image edges will appear in the residuum image as a pair of line-like structures, one with positive intensities, the other with negative intensities. The occurrence of such a pair can be detected and indicates, e.g. an increased elasticity or a decreased weight of the regularizer or an increased weight of the similarity term or a pre-processing of the images. In combination with other measures, e.g. the intensity histogram, within the same image region, dedicated pre-processing is possible, e.g. via a mapping of the intensities in order to enhance the strength of the edge under consideration. The presence of structures in the residuum image can also suggest a larger number of iteration levels or the registration on a refined resolution level.

As another example, based on a segmentation result the anatomical position of the ROI can be used for parameter setting. Based on the segmentation result, an organ-specific or bone-specific parameter setting can be used.

One or multiple of the aforementioned examples can be combined with an analysis on multiple resolution levels (or multiple scales). If a certain feature is not present after evaluation on a certain image resolution level but is present on a finer image resolution level, it is reasonable to choose a parameter setting which adds the finer resolution level to the registration.

The selection of the ROI may be done manually by a user, for example with the help of a mouse or some other pointer with which the user can indicate boundaries of the desired ROI on a display of the images. In another embodiment, selection of the ROI may be done automatically, for example based on an algorithm that segments regions with particular features in a given image.

The at least one local registration of the images within the selected ROI using the given registration algorithm with a different parameter vector can optionally be repeated at least once. One cycle of local registrations may for example allow for a selection of the best result by a user, and the following cycle of local registrations may be based on this selection, using for example parameter vectors close to the one that was selected in the previous cycle. Of course this process may be iterated several times.

In the embodiments of the method and the image processing device, one local registration for the ROI may be considered as the final local registration (e.g. the local registration that has been selected as the best one by a user, or the local registration that is based on an automatically determined parameter vector). To achieve an optimal overall registration of the input images, it is preferred that this final local registration is merged with the global registration. Such a merging may be achieved in various ways as long as it is provided that the final local registration dominates (or exclusively applies) within the ROI while the global registration dominates (or exclusively applies) outside the ROI. Near the boundary of the ROI, a transition region may be defined in which a continuous blending from the global registration to the local registration takes place (cf. US 2013/0182925 A1).

The global registration and/or the local registration(s) may preferably be non-rigid registrations (or "free-form transformations"). Non-rigid registrations can usually better map two images onto each other, particularly if they depict soft, deformable material such as body tissue.

Depending on the given registration algorithm, the associated parameter vectors may contain a variety of different types of parameters. In a preferred embodiment, the parameter vector comprises at least one parameter selected from the group consisting of: a material property, a weighting factor, a number of iterations, and an image resolution. A typical parameter vector may for example comprise several material properties (e.g. elasticity of bones and muscles), a weighting factor (e.g. of image similarity vs. regularization), a maximal number of iterations, and a (sub-optimal) resolution of the images used for the local registration.

The images that are registered may for example be images generated by an X-ray device such as an X ray projection apparatus or a CT scanner. Additionally or alternatively, the images may have been generated by a PET (Positron Emission Tomography) or SPECT (Single Photon Emission Computed Tomography) device, a Magnetic Resonance Imaging (MRI) device, or an ultrasound (US) device.

The described method will typically be realized with the help of a computing device, e.g. a microprocessor or an FPGA in the image processing device. Accordingly, the present invention further includes a computer program product which provides the functionality of any of the methods according to the present invention when executed on a computing device.

Further, the present invention includes a data carrier, for example a floppy disk, a hard disk, an EPROM, a compact disc (CD-ROM), a digital versatile disc (DVD), or a USB stick which stores the computer product in a machine readable form and which executes at least one of the methods of the invention when the program stored on the data carrier is executed on a computing device. The data carrier may particularly be suited for storing the program of the computing device mentioned in the previous paragraph.

Nowadays, such software is often offered on the Internet or a company Intranet for download, hence the present invention also includes transmitting the computer product according to the present invention over a local or wide area network.

BRIEF DESCRIPTION OF THE DRAWINGS

These and other aspects of the invention will be apparent from and elucidated with reference to the embodiments described hereinafter.

In the drawings.

Like reference numbers refer in the Figures to identical or similar components.

DETAILED DESCRIPTION OF EMBODIMENTS

Image registration is increasingly accepted as base technology to establish correspondences between images. The application range is broad, covering frequent applications such as dynamic contrast imaging and change quantification in follow-up studies. Rigid/affine registration is suited only for few applications, and the majority of applications requires non-rigid registration.

It is always desirable to improve the accuracy of registrations, in particular if low-contrast structures or strongly moving structures have to be aligned. According to an approach that is proposed here, modified registration parameters are used to achieve such improvements. As their choice can however be challenging and require expert knowledge, a user-friendly way to modify registration parameters in a what-you-see-is-what-you-get fashion is provided.

Figure 1:
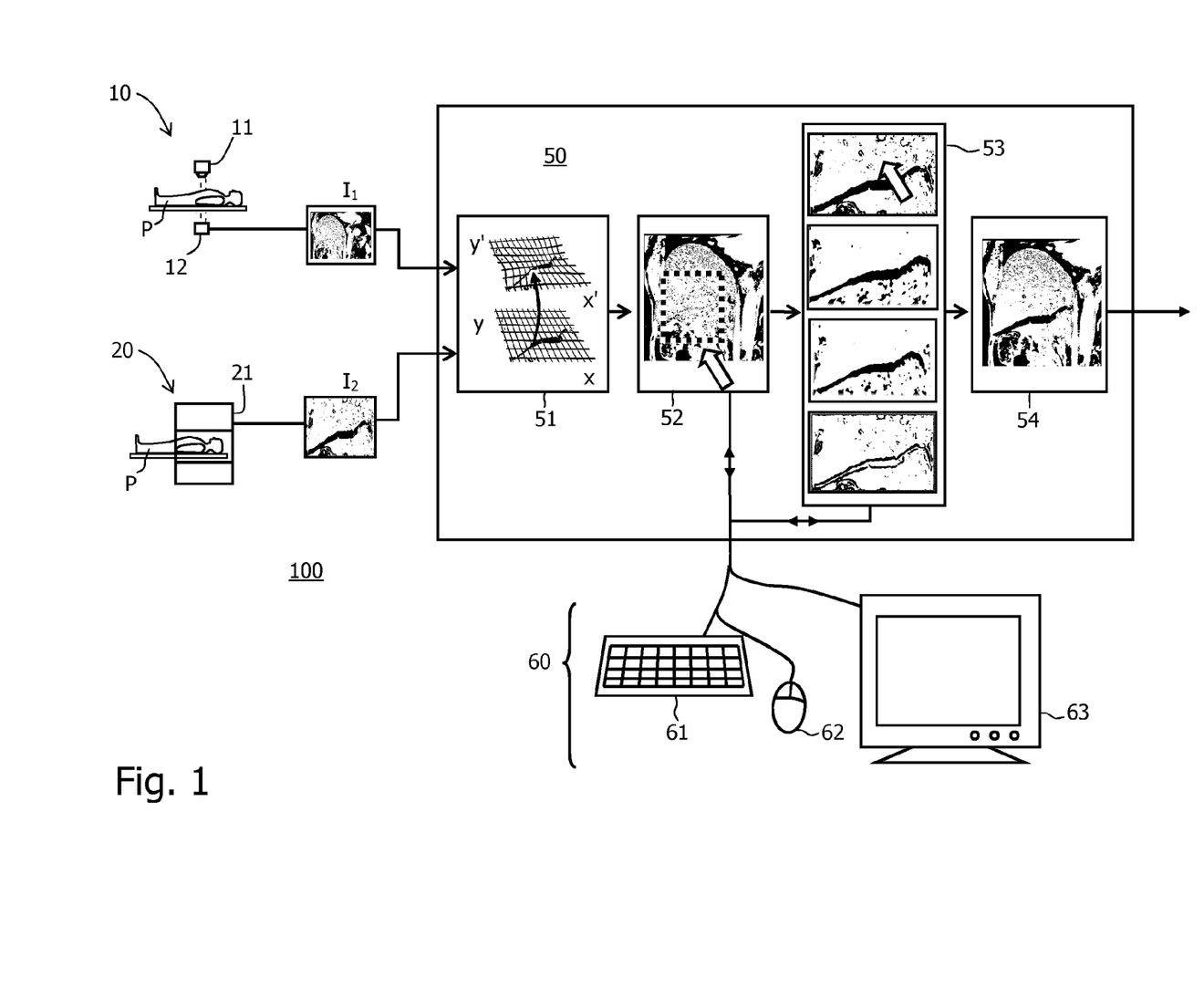
FIG. 1 schematically shows a medical imaging apparatus according to an embodiment of the invention.

FIG. 1 schematically illustrates a medical imaging apparatus 100 according to an embodiment of above approach. A central element of the imaging apparatus is an image processing device 50 that may for example be realized by a microcomputer with associated software. The boxes that are depicted within the image processing device 50 are rather meant to illustrate different processing steps than different hardware components. Typically, these boxes correspond to modules which are primarily implemented by associated software (sub-)routines.

Input images $I_1$, $I_2$ are supplied to the image processing device 50 that may in general originate from any appropriate image source, including a storage in which previously generated images are stored for later processing. In the shown example, a first image $I_1$ (or a stream of images) is provided by an X-ray scanner 10 with an X-ray source 11 and a detector 12 that can rotate about a patient P on a patient table. A second image $I_2$ (or a stream of images) is provided by an MRI scanner 20 that can generate sectional images or 3D images of the body of a patient P located in the bore of the scanner.

The first and second images $I_1$, $I_2$ are provided in this example by different imaging modalities. The dimensionality of the images (2D, 3D) may be the same or different. Moreover, the same object, for example the same part of the body of a patient P, will have to be depicted on the supplied images $I_1$, $I_2$ to allow for a reasonable registration.

In the image processing device 50, the two (or more) images $I_1$, $I_2$ provided by external means are first processed in a "global registration module" 51 (optional preprocessing steps such as filtering or the removal of non-interesting image parts are not shown in detail here). The global registration module 51 executes a global registration GR of the images $I_1$, $I_2$ using some given registration algorithm that makes use of a (given) first parameter vector $p_0$. As indicated in the box of this module, the global registration usually provides a mapping f of the coordinates x, y, z of the first image $I_1$ onto the coordinates x', y', z' of the second image I₂. This mapping is such that, for example, a point x, y, z which corresponds to a particular location or structure in the first image I₁ (e.g. a bifurcation of a vessel) is mapped onto the point x', y', z' which corresponds to the same location or structure in the second image I₂. In the drawing, this mapping is illustrated by a deformation of the x', y', z'-coordinate system of the second image I₂ (such that identical object locations/structures in the two images coincide if the first and the deformed second image are superposed).

The result of the global registration is next passed on to a "selection module" 52 that allows for the selection of a region of interest ("ROI") by a user. This step makes use of an external user interface 60 to display the globally registered images on a display or monitor 63 and to allow for the indication of the ROI by the user with the help of a keyboard 61 and a mouse 62.

It should be noted that other ways for selecting the ROI are possible, too. Thus the selection may for example be based on one of the original images (or on both), or the selection may be done automatically by the processing device 50.

After selection of the ROI, several local registrations LR1, . . . LRs, . . . LRn are executed within the ROI by a "local registration module" 53. Each of these local registrations applies the same registration algorithm that was used by the global registration module, but uses a different parameter vector $p_1 \neq p_2 \neq \ldots p_s \neq \ldots p_n$.

The results of the aforementioned local registrations LR1, . . . LRs, . . . LRn are presented to the user on the monitor 63. Preferably, all results are shown in parallel and optionally together with the result of the global registration GR at the center. The user may then select one or more of these local registrations, for example the local registration LRs, that he/she considers to be the best. This selected local registration LRs may optionally be improved by a refinement, e.g. a calculation with higher resolution, before it is further processed.

The local registration LRs selected by the user (or, in fact, the corresponding parameter vector $p_s$) is forwarded to a "merging module" 54 in which it is merged with the global registration GR in an appropriate way to yield a final overall registration. The global registration GR may for example dominate the final overall registration outside the ROI, while the selected local registration LRs dominates inside the ROI with a continuous, soft transition from the inside to the outside of the ROI. The final overall registration is then typically made available for further processing, storage and/or evaluation.

As an alternative to the calculation of several local registrations (LR1, . . . LRs, . . . LRn) with different parameter vectors $(p_1, \ldots p_s, \ldots p_n)$ and to the selection of a best local registration (LRs) by a user, the ROI may automatically be analyzed to find a parameter vector $p_s$ for a subsequent local registration.

The given registration algorithm that is applied in the global and the local registration modules 51, 53 may preferably be a non-rigid registration. A non-rigid image registration may be implemented as an iterative process in which an image similarity term is optimized, while an additional regularization term keeps the solution in some sense realistic (usually a certain smoothness of the resulting deformation field is wanted). A typical non-rigid registration scheme consists of the following ingredients:

A representation and parameterization of the mapping between two or more image domains. Frequent choices are, e.g., grid of B-Spline control points, or image voxel wise translation vectors.

An objective function combining an image similarity term and a regularization term. Frequent choices for the similarity term are mutual information, sum of squared differences, or intensity correlation. The regularization term usually implies a certain degree of smoothness, by, e.g., penalizing first- and/or second-order derivatives of the mapping field.

Image similarity and regularization term are weighted depending on methodological choices, image modality, and application. Weighting is usually fixed for the whole image.

A set (or vector) of parameters used to steer the registration scheme (e.g. elasticity/material properties, weighting factors, maximum number of iterations, resolution levels to be used etc.).

An optimization scheme, e.g., gradient descend, conjugate gradients, etc.

The accuracy of the registration output depends on (i) the number of iterations spent, i.e. on the runtime, (ii) the parameter setting used for registration, and (iii) the anatomy of interest. Since for non-rigid image registration no automatic validation scheme exists, it cannot be automatically determined if a registration output fulfills the user specifications (e.g., "registration error below 2 mm"). Even for a large number of iterations it cannot be guaranteed that the user specifications are fulfilled for any anatomy of interest.

Figure 2:
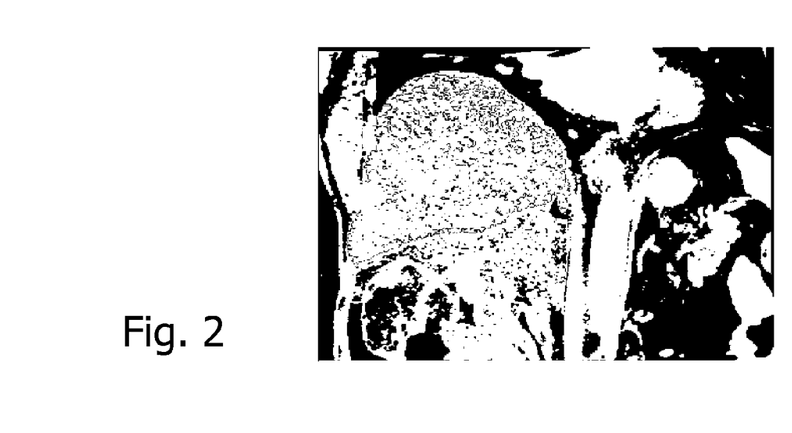
FIG. 2 shows an example of an input image.

FIG. 2 shows for example an exemplary CT image in which high-contrasted image edges (e.g. the diaphragm) are easier to detect than low-contrasted image edges (e.g., the lower boundary of the liver). By this, any registration scheme tends to align high-contrasted image edges better than low-contrasted ones.

Moreover, bone structures may for example get unrealistically deformed when using a tissue-specific parameter setting and require a bone-specific setting of the modeled material properties. In addition, different application scenarios (point tracking, change quantification in follow-up studies, perfusion studies, (dynamic) contrast imaging, etc.) pose different requirements, and there does not exist a one-solves-it-all registration solution.

By introducing the refinement in a ROI proposed above as a post-processing step, the accuracy of the registration output can however be improved by means of minimal user input.

Figure 3:
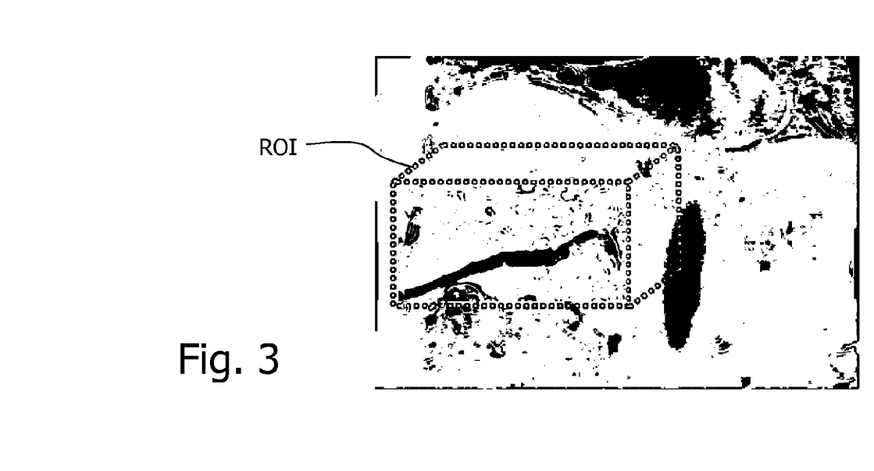
FIG. 3 illustrates the selection of a ROI in two globally registered input images.

As explained above, said refinement requires the selection of a region of interest ROI in one of the input images. FIG. 3 illustrates the display of the result of the global registration as residuum (i.e. subtraction of first image and deformed second image) in which a cuboid has been selected as ROI to indicate the region where the registration output needs to be improved (lower liver boundary is not aligned). Other possible forms of the ROI comprise for example a sphere, an ellipsoid, or an irregular shape.

Figure 4:
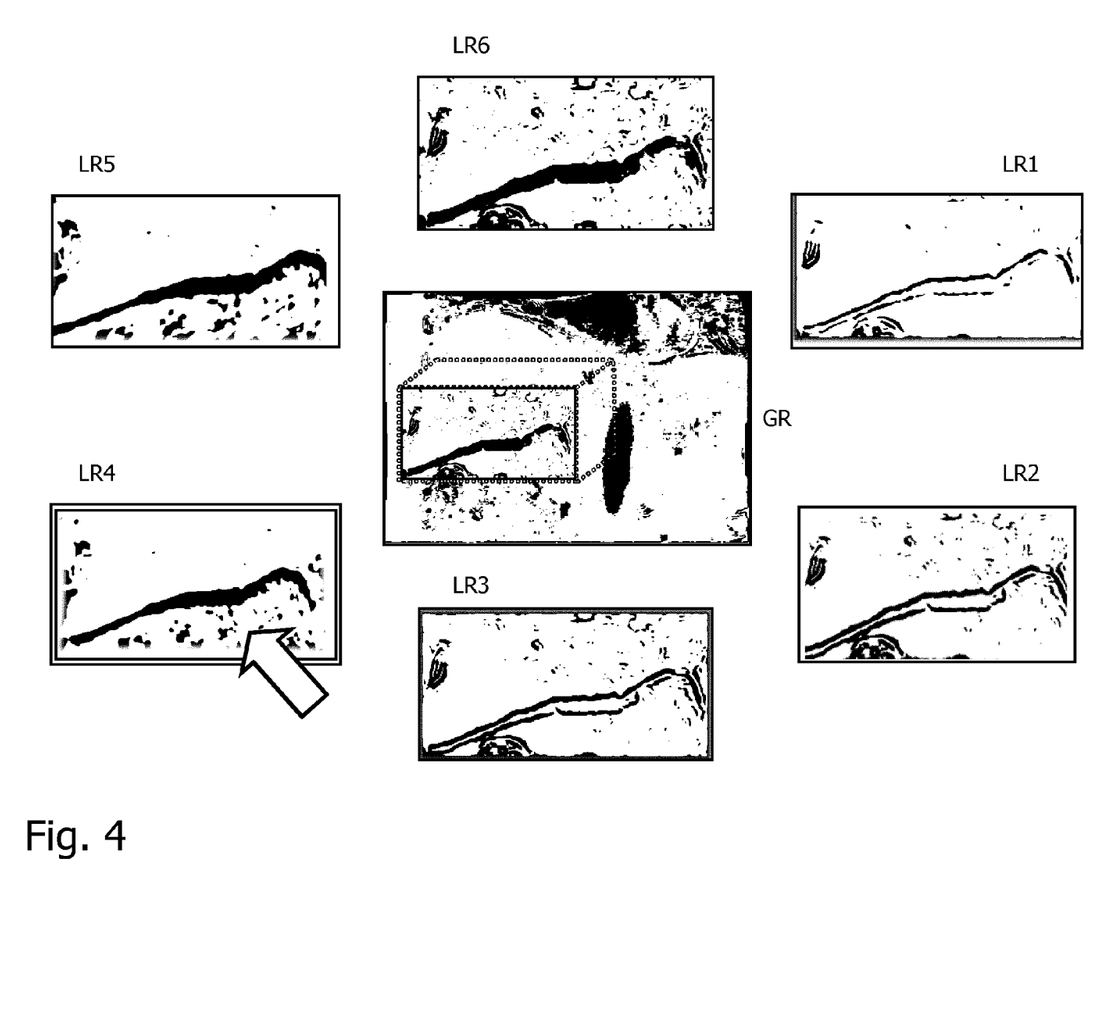
FIG. 4 illustrates the display of a global registration and a plurality of local registrations with different parameter vectors.

Multiple fast local registration refinements LR1, . . . LRn (with different parameter settings) are next computed for the ROI and presented to the user. As illustrated in FIG. 4, this may for instance be done in the form of previews displayed around a representation of the global registration GR at the center. Following a what-you-see-is-what-you-get approach the user can then select the preview best satisfying his/her needs (and hereby selects a parameter setting). This may be followed by an accurate registration refinement with the new parameter setting. The only required user input thus is (i) selecting a region of interest, and (ii) selecting one of the (very fast) computed previews.

The main prerequisites and steps of the described approach are:
1. Provision of two or more medical images $I_1$, $I_2$ of arbitrary dimension.
2. Execution of a (preferably non-rigid) image registration algorithm with a standard parameter setting $p_0$, using for example an image similarity and a regularization term in order to align the input images.
3. Provision of a first graphical user interface (GUI) where the first, global registration output is shown to the user and where the user can select a ROI in order to indicate the image region where the registration output needs to be improved. Representation of the output may for example be done by overlaying the first image with an aligned (deformed) second image ("fusion"), or by computing the subtraction of the first image and a deformed second image ("residuum"), or by overlaying the image edges extracted from a deformed second image onto the first image ("contour overlay").
4. Determination of a variety of modified parameter settings $p_1, \ldots p_s, \ldots p_n$ used for a very fast refined, local image registration of the ROI. In this step, parameters used in the global registration algorithm are modified in a reasonable manner, e.g. the modeled elasticity parameters are increased or decreased, tissue interfaces are highlighted by an intensity mapping algorithm or a histogram equalization, or a different similarity measure or regularizer is chosen. Parameter modification results in a set of new parameter settings.

Moreover, the global registration algorithm from step 2 is re-run with the input images $I_1$, $I_2$ cropped by the user-defined ROI and with each of the new parameter settings $p_1, \ldots p_s, \ldots p_n$. The registration algorithm can be initialized with the global deformation obtained in step 2.

In the interest of an interactive processing the execution of the local registration algorithm needs to be fast. This can be achieved by (i) restricting the registration domain to the ROI, and (ii) restricting the registration to coarse (i.e. downsampled) resolutions of the input images (the result is then interpreted as a preview of the precise registration output). For each parameter setting a deformation for the ROI is computed.
5. Provision of a second GUI where again the first, global registration output as well as the collection of refined, local registration outputs (previews) are shown to the user and where the user can select the preview which best fulfills his/her needs. Due to the preview-state (i.e. the registration performed in a very fast mode) it might occur that the alignment is still non-perfect. However, it is only important to select the preview (with the corresponding parameter setting) which improves the global registration result (from step 2) in the expected way/direction.
6. The selected parameter setting $p_s$ is then used to perform a refined registration, i.e. initialized by the global deformation obtained in step 2. A highly-accurate registration with the new parameter setting is executed for the ROI. In order to maintain a smooth deformation across the ROI boundary, appropriate boundary conditions have to be chosen for the refined registration. Output of the system are aligned images or deformation fields between some or all of the input images.

With the above means a GUI with two-click user interaction for an additional refinement as a post-processing step can be realized. Optional modifications and extensions of the described procedure are for example:

The repetition of steps 3 (ROI-selection) to 6 (refined registration) in a "loop" until the user is satisfied with the registration accuracy.

Storage of the user selection. Favorite selection(s) may then later be proposed to (i) reduce number of refinement steps and/or (ii) restrict the set of modified parameter settings.

The user may select the second-best (third-best, etc.) preview as well. The search range may then be spanned by the parameter settings from the n best previews (weighted according to the user ranking). This can further improve the parameter setting used for the refined registration in step 6.

In summary, embodiments of image registration have been described in which modified registration parameters can improve registration accuracy, especially locally. The approach allows adaptation of registration parameters in a what-you-see-is-what-you-get fashion. It requires no expert knowledge and minimal user input (2 clicks).

The procedure described above is based on the observation that registration parameters are usually chosen once for the entire image domain, but that within a certain region of interest (ROI) a modified parameter setting may be more suitable and can improve the registration output locally. In an alternative approach that makes use of this observation an automatic analysis of the image content within a ROI (e.g. around a user-clicked position) is proposed which triggers an ensuing second-pass registration with an automatically determined modified parameter setting.

The main prerequisites and steps of this alternative approach are:
1. Two or more medical images of arbitrary dimension (as above).
2. An e.g. non-rigid global image registration algorithm with a standard parameter setting, using for example an image similarity and a regularization term (as above).
3. A GUI where the first global registration output is shown to the user (e.g., in terms of fused images, residuum, contour overlay) and where the user can select a position or a ROI (as above).
4. An automatic analysis of the image content within the ROI determines a more suitable parameter setting from a range of stored setups. The automatic analysis could for example employ intensity ranges, image edges, entropy measurements, intensity histograms, edge histograms, intensity range of residuum, anatomical position (in combination with a prior segmentation). A low intensity range, for example, will motivate histogram equalization in order to facilitate alignment of low-contrasted image structures. The presence of filigree structures in the ROI, for example, calls for the usage of a higher image resolution than usually used.
5. The modified parameter setting is used to perform a second-pass (local) registration, i.e. initialized by the global deformation obtained in step 2, a highly-accurate registration with the new parameter setting is executed for the ROI. In order to maintain a smooth deformation across the ROI boundary, appropriate boundary conditions have to be chosen for the refined registration. Output of the system are aligned images or deformation fields between some or all of the input images.

Hence a fully-automatic analysis is achieved that is driven by user guidance (single click on image region where registration accuracy needs to be improved). The analysis is based on (i) the image content of both input images, and (ii) a first-pass global registration result; it is performed within a region around a user-specified position. The fully-automatic analysis results in a modified parameter setting, which is then used for a second-pass registration.

The procedures explained above can be applied for the processing of image data from CT or any other imaging modality.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An image processing device that registers at least two images of an object, comprising:
   a processor configured:
      to execute a global registration of the at least images using a given registration algorithm with a first parameter vector;
      to select of a region of interest (ROI) in the images; and
      to execute at least one local registration of the at least images within the selected ROI using the given registration algorithm with a different parameter vector;
   wherein a parameter vector is determined for at least one local registration based on an automatic analysis of the ROI which comprises the evaluation of:
   intensity ranges,
   intensity histograms,
   image edges,
   edge histograms,
   entropy measurements,
   intensity range of residuum,
   and/or anatomical position.

2. A medical imaging apparatus, comprising:
   at least one imaging scanner for generating images of an object;
   the image processing device according to claim 1 for the registration of images provided by the imaging scanner.

3. The medical imaging apparatus of claim 2, wherein at least two local registrations are executed with different parameter vectors.

4. The medical imaging apparatus of claim 2, wherein the automatic analysis of the ROI comprises the evaluation of:
   intensity ranges with respect to an anatomical content that indicates a preferred parameter vector,
   image edges with respect to edges of smaller strength that require a parameter vector to enhance their strength,
   intensity range of residuum with respect to the occurrence of pairs of positive and negative intensities,
   and/or anatomical position with respect to the anatomical position of the ROI indicating an organ-specific or bone-specific parameter vector.

5. The medical imaging apparatus of claim 2, wherein the ROI is automatically selected.

6. The medical imaging apparatus of claim 2, wherein the global registration and at least one of the local registrations are merged.

7. The medical imaging apparatus of claim 2, wherein the global registration and the local registration are non-rigid registrations.

8. The medical imaging apparatus of claim 2, wherein the parameter vectors comprise at least one parameter selected from the group consisting of a material property, a weighting factor, a number of iterations, and an image resolution.

9. The medical imaging apparatus of claim 2, wherein the images are generated by one of an X ray device, a CT scanner, an MR scanner, a PET scanner, a SPECT scanner, or an ultrasound device.

10. The image processing device of claim 1 wherein at least two local registrations are executed with different parameter vectors.

11. The image processing device of claim 10, wherein the results of said local registrations are displayed and that a user can select at least one of the displayed local registrations.

12. The image processing device of claim 11, wherein the selected local registration is refined.

13. The image processing device of claim 10, wherein user's selections are evaluated with respect to the user's preferences.

14. The image processing device of claim 1, wherein the automatic analysis of the ROI comprises the evaluation of:
   intensity ranges with respect to an anatomical content that indicates a preferred parameter vector,
   image edges with respect to edges of smaller strength that require a parameter vector to enhance their strength,
   intensity range of residuum with respect to the occurrence of pairs of positive and negative intensities,
   and/or anatomical position with respect to the anatomical position of the ROI indicating an organ-specific or bone-specific parameter vector.

15. The image processing device of claim 1, wherein the ROI is automatically selected.

16. The image processing device of claim 1, wherein the global registration and at least one of the local registrations are merged.

17. The image processing device of claim 1, wherein the global registration and the local registration are non-rigid registrations.

18. The image processing device of claim 1, wherein the parameter vectors comprise at least one parameter selected from the group consisting of a material property, a weighting factor, a number of iterations, and an image resolution.

19. The image processing device of claim 1, wherein the images are generated by one of an X ray device, a CT scanner, an MRI scanner, a PET scanner, a SPECT scanner, or an ultrasound device.

20. A method for a registration of at least two images of an object, said method comprising:
   a) a "global registration" of the at least two images using a given registration algorithm with a first parameter vector;
   b) a selection of a region of interest (ROI) in the at least two images;
   c) at least one "local registration" of the at least two images within the selected ROI using the given registration algorithm with a different parameter vector;

wherein a parameter vector is determined for at least one local registration based on an automatic analysis of the ROI which comprises the evaluation of:
intensity ranges,
intensity histograms,
image edges,
edge histograms,
entropy measurements,
intensity range of residuum,
and/or anatomical position.

21. The method of claim 20,
wherein step c) is repeated at least once.

22. The method of claim 20,
wherein at least two local registrations are executed with different parameter vectors.

23. The method of claim 20,
wherein the automatic analysis of the ROI comprises the evaluation of:
intensity ranges with respect to an anatomical content that indicates a preferred parameter vector,
image edges with respect to edges of smaller strength that require a parameter vector to enhance their strength,
intensity range of residuum with respect to the occurrence of pairs of positive and negative intensities,
and/or anatomical position with respect to the anatomical position of the ROI indicating an organ-specific or bone-specific parameter vector.

24. The method of claim 20,
wherein the ROI is automatically selected.

25. The method of claim 20,
wherein the global registration and at least one of the local registrations are merged.

26. The method of claim 20,
wherein the global registration and the local registration are non-rigid registrations.

27. The method of claim 20,
wherein the parameter vectors comprise at least one parameter selected from the group consisting of a material property, a weighting factor, a number of iterations, and an image resolution.

28. The method of claim 20,
wherein the images are generated by one of an X ray device, a CT scanner, an MR scanner, a PET scanner, a SPECT scanner, or an ultrasound device.

* * * * *